United States Patent [19]

Welker

[11] Patent Number: 4,557,151

[45] Date of Patent: Dec. 10, 1985

[54] SAMPLER INCORPORATING PRESSURE BALANCED CHECK VALVE

[75] Inventor: Robert H. Welker, Sugar Land, Tex.

[73] Assignee: Welker Engineering Company, Sugar Land, Tex.

[21] Appl. No.: 456,328

[22] Filed: Jan. 7, 1983

[51] Int. Cl.[4] .............................................. G01N 1/14
[52] U.S. Cl. .................................................. 73/863.84
[58] Field of Search ............. 73/863.71, 863.72, 863.73, 73/863.81, 863.82, 863.83, 863.84, 863.85, 863.86, 864.34, 864.63, 864.73, 864.74

[56] References Cited

U.S. PATENT DOCUMENTS

| 3,074,425 | 1/1963 | Kikendall | 251/332 |
| 3,412,613 | 11/1968 | Brown et al. | 73/864.74 |
| 3,812,722 | 5/1974 | Soudelier | 73/863.84 |
| 4,350,051 | 9/1982 | Thompson | 73/864.74 |
| 4,372,382 | 2/1983 | Rooney et al. | 73/864.63 |
| 4,403,518 | 9/1983 | Welker | 73/864.34 |

FOREIGN PATENT DOCUMENTS 2094266 9/1982 United Kingdom .

OTHER PUBLICATIONS

Series 200 Grab Sampler (a sales brochure), Jiskoot Auto-Control L.T.D., Tunbridge Wells.Kent.TN2DJ, England.

Primary Examiner—S. Clement Swisher
Attorney, Agent, or Firm—Gunn, Lee & Jackson

[57] ABSTRACT

A sampling apparatus having a pressure balanced check valve is set forth in the preferred and illustrated embodiment. The sampling system includes an elongate probe which is driven by a diaphragm motor. The probe extends through a fixed housing and terminates at a sample collection head. The probe is provided with a lengthwise passage in it. Sample is collected from a pumping apparatus comprising a reciprocating anvil and a fixed hammer. These two unyielding members are reciprocated toward one another. They capture, therebetween, a resilient plug having a dished area which collapses on pressure. This forces sample from the dished area. It flows into a passage, into the probe, through a check valve. The check valve is pressure balanced so that the force required to overcome it is not dependent on line pressure, sample collection container back pressure and the like. Dead volume is reduced to an absolute minimum.

6 Claims, 3 Drawing Figures

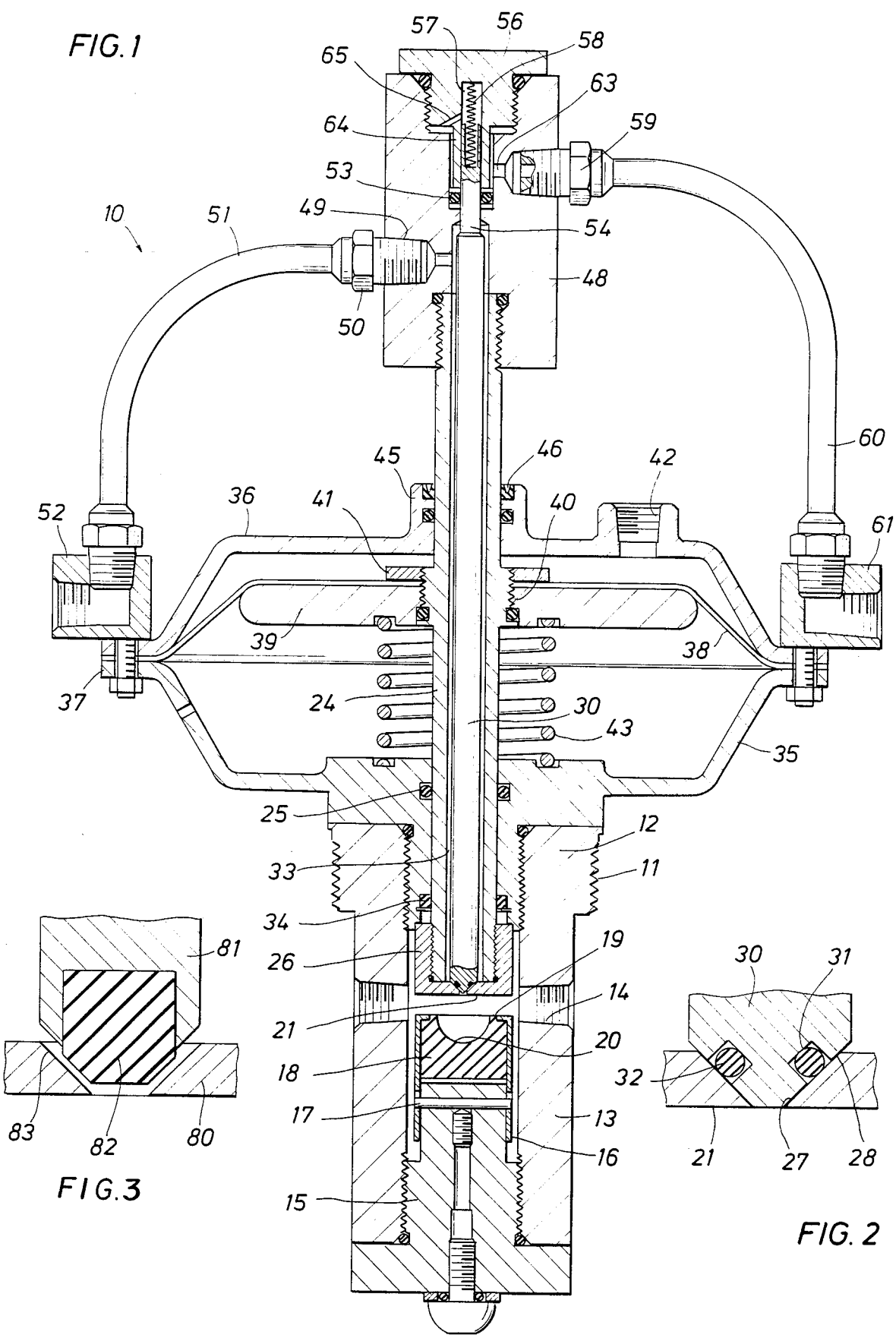

SAMPLER INCORPORATING PRESSURE BALANCED CHECK VALVE

BACKGROUND OF THE DISCLOSURE

U.S. Pat. No. 3,945,770, of this inventor, discloses a high pressure pump. That pump describes a solid, nonyielding reciprocating member. It reciprocates towards an opposing resilient plug. The plug is supported by a nonyielding member also. The resilient plug incorporates a dished area which collapses on pressing the components together and the squeeze created by this collapse forces gas or liquid, captured in the dished area, through a passage. This disclosure sets forth an improved passage construction. The reciprocating member must terminate in a solid face, and the solid face is ordinarily constructed by fabricating a threaded cap. The threaded cap has a specific wall thickness, and a thin passage is drilled through this wall to center at the dished area. This is the outlet path. This passage has a finite volume which is a dead volume. That is, the dished area can be collapsed on application of pressure until there is no remaining volume in the dished area. The sample which is forced from the dished area must be forced through the narrow passage. This is a dead volume, namely the volume of the passage. The passage ordinarily terminates at a check valve to prevent back flow. The check valve is ordinarily arranged at the end of the passage, but it nevertheless cannot prevent the passage from collecting a dead volume which is not evacuated on each stroke of the sample collection apparatus.

An alternate form of sample collection apparatus uses a movable piston which reciprocates in a cylinder to admit the sample; the piston is forced along the cylinder to pressurize the sample to flow into a passage and through a check valve.

By contrast, this apparatus sets forth an improved passage construction. It is particularly improved in that the volume of the passage is substantially reduced. This construction substantially eliminates the dead volume in the passage. It is accomplished by positioning a check valve element in the altered passage which extends to the face of the anvil. That is to say, there is no passage volume left when the check valve is in position. The check valve can be forced open so that the passage permits flow in the intended manner; when it is closed, it closes fully and substantially fills the passage so that the check valve element is flush with the face of the anvil for all practical purposes.

The reduction of the fluid passage dead volume to a zero value enables collection of all of the sample which is captured by the device. It, thereby, enables the device to collect the sample volume more accurately. As the sample is collected, it must be forced pass a check valve. Some type of check valve arrangement is required to prevent the sample from trickling back out of the sample collection apparatus. One kind of check valve is a spring forcing a ball valve element against a seat, and this has worked quite well. An alternate form of check valve element utilizes an elongate pin with large shoulder to seat against the back face of the anvil wherein the pin protrudes into the passage to guide and align the check valve element. This again uses a return spring.

The return spring is a relatively small spring located in a relatively small chamber. Such a small spring can only, of necessity, provide a relatively small thrust. The force applied by the spring against the valve element, when considered in the abstract, should be sufficient to simply hold the valve closed. However, pressure variations in the sample collection system and the pipeline pose problems for the spring. Assume that the spring asserts a force sufficient to hold the check valve closed against the normal operating pressure in the pipeline and assume that is a value of 500 psi. Assume that the pipeline is designed for a maximum pressure of 800 psi. While the pressure will normally be maintained around 500 psi by the ordinary operation of the pipeline, inevitably, pressure surges will occur in the pipeline. Assume that a pressure surge transit occurs which increases the pressure to 750 psi for five seconds. In that event, the check valve spring will be overcome and sample will be forced continuously pass the check valve into the sample collection apparatus. This can be overcome by utilizing a spring of sufficient strength to overcome 800 psi, the rating of the pipeline. However, such springs must inevitably be larger to provide the increased spring force. There is a constraint on space, and it is not easy to provide such a strong spring for incorporation in such a small space.

The spring force necessary to overcome such high pressures in the pipeline is further aggravated by the back pressure in the sample collection system. The sample collection system has a back pressure normally associated with the sample collection system. The sample collected by the sample collection apparatus must ordinarily be removed from the sample collection device through a tubing into a sample collection bottle. The difference in sample collection bottles pose a problem for the sample collection apparatus. Consider the following three exemplarly sample collection bottles. Assume simply that the sample collection line is placed in a bucket to collect a sample, in which event, the back pressure is atmospheric pressure. That, at least, provides a relatively constant and low back pressure in the sample collection system. There are other sample collection bottles which are closed chambers. The first portion of collected sample is collected at atmospheric back pressure. However, the sample collection bottle does not have a vent, and the pressure within the bottle increases. The pressure may well increase to an extremely high pressure, and this high back pressure is a force added to the spring acting on the check valve. This inevitably creates a different set or trip point at which the check valve opens. A third type of sample collection bottle is one which provides a relatively constant back pressure. This can be treated as the atmospheric back pressure sample collection bottle described above. While it may be not be atmospheric, the pressure is at least fixed or relatively constant.

A relatively constant back pressure thus equates to an additional constant force acting on the check valve.

Pipeline pressure is not perfectly regulated. As pipeline pressure increases, it may reach the point at which the diaphragm motor of the apparatus cannot overcome pipeline pressure. Consider the situation wherein the movable portion of the probe in the sample collection apparatus has a circular area of one square inch and works into a pipeline having a nominal pressure of 500 psi. In this example, 500 pounds of force are required to overcome pipeline pressure. This ignores the force which is required to operate the sample collection probe. Consider the situation in which the pipeline pressure increases to 1,000 psi whereupon 1,000 pounds of force are required to overcome the resistive pressure to operate of the probe. Ordinarily, the device is powered by a diaphragm motor. This device is normally operated at relatively low pressures. If the surface area is twenty-five square inches, only about twenty psi is required at the diaphragm motor to overcome the resistive force preventing insertion of the probe into the pipeline. This leaves substantial force available to compress the resilient plug and operate the sample collection apparatus. However, assume that pipeline pressure is 1,000 psi in which event 1,000 pounds of force, or a pressure of 40 psi in the diaphragm motor is required to simply overcome pipeline pressure. This leaves very little force available to compress the resilient plug to operate the sample collection apparatus.

The present apparatus overcomes this difficulty. In fact, many advantages flow from the incorporation of a pressure balanced check valve. The check valve element is a fairly large telescoping member on the interior of the probe. The lower end is exposed to pipeline pressure. Pipeline pressure is routed through a conduit to the top end of the check valve element and applied there also. The relative cross-sectional area of the two surfaces exposed to the pipeline pressure are made approximately equal so that the check valve element is pressure balanced. Thus, increases or decreases in pipeline pressure simply null by forming relatively equal and opposite forces acting on the check valve element. Then, a small spring can be used to force the check valve element to the closed position, and this spring need never be changed or recalibrated to compensate for operating pressures on the sample collection apparatus. In fact, if the device is installed in the vertical position and sufficient weight is placed on the check valve element, the weight will serve as a return force. By contrast, the device can be operated horizontally or even in an inverted position by simply installing a spring calibrated to overcome the weight of the equipment to force it to the closed condition. The spring, which is thus described, need not overcome pressure differential created forces acting on the check valve element. This has the advantage of operating even with great fluctuations in pipeline pressure. It also is immune to variations in back pressure. Back pressure increases in the probe do not act on the cross-sectional areas of the probe and, therefore, do not upset this relative balance on the check valve element.

These features and others set forth hereinbelow therefore provide a device capable of operation in a wide variety of operating conditions.

BRIEF DESCRIPTION OF THE DISCLOSED APPARATUS

Briefly, this apparatus discloses a sample collection apparatus featuring a reciprocating probe section having a bottom anvil directed against a resilient plug. A very small passage through the anvil is provided, and it is plugged by the check valve element. The check valve element extends to an area where it is flush with the face of the anvil. The check valve element is an elongate member, exposed to pipeline pressure at both ends and is therefore substantially free and independent of pipeline pressure variations.

BRIEF DESCRIPTION OF THE DRAWINGS

So that the manner in which the above recited features, advantages and objects of the invention, as well as others, which will become apparent, are attained and can be understood in detail, a more particular description of the invention, briefly summarized above, may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

FIG. 1 is a sectional view through an improved sample collection apparatus in accordance with the disclosures herein including a pressure balanced check valve element within the probe;

FIG. 2 is an enlarged detail view of the lower tip of the check valve element and cooperative opening showing a reduced dead volume passage; and FIG. 3 is an alternate construction of the lower tip of the check valve element.

DETAILED DESCRIPTION OF THE PREFERRED EMBODIMENT

Attention is directed to the sample collection apparatus 10 shown in FIG. 1. This shows, in sectional view, the entire structure of the fluid sample pump system. As the description proceeds, it will develop the basic operating mode of the equipment shown thereat which follows the disclosure of U.S. Pat. No. 3,945,770 except that it includes the improvements which are described below. Those improvements are directed to an improved check valve and check valve element system including a pressure balance arrangement.

The pump system 10 incorporates an elongate wand or probe at the lower portions which is adapted to be positioned within a tank or inserted through the wall of a pipeline. To this end, a set of threads 11 is included on a lower surrounding peripheral housing 12. The pump system has a variety of mountings including threaded connection of the form shown at FIG. 1 and non-threaded cylindrical constructions. An elongate wand of cylindrical construction is fixed to the cylindrical body 12 which supports an elongate tubular sleeve 13. The sleeve 13 is provided with a set of ports 14 to admit fluid from the pipeline. That is, fluid flows into the sample collection apparatus to be gathered. The elongate sleeve 13 is joined at the upper end to the cylindrical body 12 by integral construction or threaded connection. The sleeve 13 is a fixed part of the equipment. It supports a large threaded bottom plug 15 which caps the bottom end and covers the bottom, and also supports an upstanding sleeve 16. The sleeve 16 telescopes over a cylindrical internal protruding post. That is concentric with and on the interior of the sleeve 13.

A fastening pin 17 passing through a hole diametrically drilled through the bottom plug 15 fastens the sleeve 16 in place to support a resilient plug 18. The plug 18 is concentric with the plug 15 and located on the interior of the sleeve. The sleeve has an overhanging lip at the top end to capture the resilient plug. The sleeve supports the plug and limits lateral expansion. The sleeve terminates at an encircling top lip defining a circular contact area 19 surrounding a dished cavity area 20.

The resilient plug cooperates with an anvil formed of a metal cap which reciprocates towards the resilient plug. The plug faces the metal cap, and the metal cap has a circular face 21 which contacts against it. This seals against the lip 19 surrounding the dished area. When the two parts are brought together, a seal is perfected and fluid within the dished chamber is captured.

The face 21 is mounted to reciprocate by the operative components of this equipment into contact whereby the chamber 20 is closed and sealed. This collects fluid within the chamber for evacuation through the equipment and collection subsequently.

The numeral 24 identifies an elongate reciprocating push rod which is hollow along its length. It passes through areas of different pressures, and a seal 25 is positioned around it in the body 12 to prevent leakage along the push rod 24. The push rod terminates at an enlarged threaded spool 26, the spool being joined to the lower end of the push rod and supporting the transverse face 21.

The face 21 is part of the spool 26 which is made of metal and which is, therefore, an unyielding material. The resilient plug 18 is supported on the nonyielding plug 15 therebelow. When the two members are brought together, the resilient plug collapses. Dependent on axial loading, pumping action is initiated by collapse of the resilient plug 18 when the push rod 24 forces the face 21 against the resilient plug. Fluid in the chamber or cavity 20 is evacuated through the improved passage to be described.

This passage is best illustrated by referring to FIG. 2. There, the face 21 is illustrated as having a small opening at 27. This opening is not a conventional drilled hole. Rather, it tapers at 28 on the opposite face and thereby describes a tapered passage. The drilled area at 28 inscribes a certain angle, and a check valve element 30 having a matching angle seats agaist the angled conic hole. The check valve element incorporates a groove 31, and a seal ring 32 is positioned in the groove.

Returning now to FIG. 1, it will be observed that an annular space 33 extends along the length of the push rod 24. The check valve element 30 is shown in FIG. 1 to be an elongate rod of significant length, terminating at the pointed lower end conforming with the drilled hole at 28. This conformance enables the very tip of the push rod 30 to extend to a point where it is flush with the face 21. The path for fluid pumped from the cavity 20 is through the opening 27 and pass the check valve element 30. This is accomplished when the check valve element is forced upwardly, clearing the seal 32 and permitting fluid flow through an annular space 33.

The check valve element 30 is an elongate rod. It is located on the interior of the push rod 24. A description of the upper portions of these components will be set forth hereinafter. For the moment, it should be noted that the push rod 24 threads to the spool 26, and a seal 34 is secured between the spool 26 and exterior of the push rod. The seal 34 includes a snap ring and seal in the groove surrounding the push rod. This prevents leakage on the exterior. The seal 34 cooperates with the seal 25 thereabove.

In the up position, there is substantial clearance between the face 21 and the resilient plug 18. Access to this area is obtained through the lateral ports 14. These ports enable fluid flow through the equipment. These ports deliver the fluid of interest to the immediate area to be captured in the cavity 20.

The push rod 24 extends through a diaphragm motor. This apparatus is formed by constructing a dish shaped lower housing 35 above the body 12, and positioning a similarly constructed upper housing 36 thereabove. The two housings join at a peripheral lip of flange 37, and suitable nuts and bolts are fastened through the flange to join the housing parts 35 and 36 together. They capture a diaphragm 38 at the flange junction of the two components, and the diaphragm isolates the interior of the housing into upper and lower chambers. The diaphragm 36 is a flexible member formed of resilient material, or alternatively, a relatively thin flexible metal typically folded with circular accordion pleats to permit flexure. The lower side of the diaphragm 38 is supported by a disk 39 which is fastened by means of threads 40 to the push rod 24. A lock ring 41 is on the top side of the diaphragm 38.

The top diaphragm housing has a tapered port 42 to permit the introduction of fluid under pressure to force the diaphragm downwardly. Downward motion compresses a coil spring 43 in the lower housing which returns the diaphragm to the up position, thereby retracting the push rod 24. The push rod 24 passes through the top housing 36 at a collar 45, the collar being provided with seals 46 to prevent leakage along the push rod.

In ordinary operation, fluid under pressure is introduced above the diaphragm and forces it downwardly. The diaphragm moves the fitting 40 and thereby reciprocates the push rod. The upper chamber is, therefore pneumatically or hydraulically filled and the lower chamber is evacuated through a suitable port or hole. The return spring 43 returns the apparatus to the raised position.

Travel of the push rod downwardly can be limited by placing a removable clamping collar around the push rod 24 at a specified elevation to travel against the upstanding collar 45, blocking further reciprocation.

A manifold block 48 is located at the top end of the push rod and is threaded to it in a leakproof connection. The manifold block is drilled with a port 49, and a fitting 50 is placed in the port. The fitting 50 connects with a flexible tubing 51 which, in turn, extends to an elbow 52 for connection with an output line. The delivered sample is provided through this line. The fitting 50 is communicated with the annular passage 33. This passage 33 is continued into the manifold block 48. The passage 33 is the sample flow path, the sample thereby flowing in this annular space and through the tubing 51.

The manifold block is drilled and countersunk to various diameters. A seal ring 53 surrounds a narrow neck 54 on the check valve element 33. The check valve element more aptly has the appearance of a long straight rod having a tapered point at one end, and supporting the narrow neck 54 at the top end. The neck 54 has a specified cross-sectional diameter. This diameter is exposed to pipeline pressure above the seal 53. It reciprocates toward a plug 56, the plug 56 threading to the manifold body 48. The plug 56 is axially drilled to define an internal chamber 57, and a small spring 58 is placed in that chamber and bears against the neck 54. It forces the check valve element toward the closed position.

A fitting 59 connects to a flexible tubing 60 which connects with an elbow 61, conveniently supported on the flange of the diaphragm housing. This enables connection to the pipeline (not shown) so that pipeline pressure can be applied to the upper end of the check valve element 30. Pipeline fluid pressure is communicated through the fitting 61, the flexible tubing 60, the fitting 59, and is introduced through a passage 63. The passage 63 opens into an annular space above the seal ring 53. The plug 56 is drilled; it has a downwardly dependent skirt 64. The skirt 64 is drilled with a small passage 65 so that fluid from the pipeline is introduced to the top end of the check valve element 30.

The pressure balance across the check valve element should be noted. In the closed condition, the force acting upwardly on the check valve element is determined by the cross-sectional area of the seal ring 32. Pipeline pressure is communicated to this area. That defines a specific area. By contrast, pipeline pressure is also applied to the upper end of the check valve element 30 to force it in the opposite direction. The area is defined by the seal ring 53. It will be observed that the two opposite ends of the check valve element are exposed to an equal pressure, and the force differential from the application of pressure at both places is determined by the differential in area. If the two areas are equal, they do not create a force differential across the check valve element.

This balanced force is very convenient. No matter what the pipeline pressure, the check valve element is maintained in a closed condition until a pumping stroke. The closed condition is sustained by gravity pulling the check valve element 30 downwardly. This pull normally occurs when it is in an upright condition. Sufficient weight tends to close the valve. This weight can be enhanced by the incorporation of the small spring 58. This spring does not work against any variable force. In other words, it does not have to be changed for a change in pipeline pressure. The spring 58 is merely a return spring which, in conjunction with the weight, acts to close the device.

The spring 58 should be increased in strength if the apparatus is inverted.

FIG. 3 discloses an alternate form of seal construction. The spool has a transverse wall 80 of suitable strength and thickness. The check valve element 81 is again an elongate rod having an end located axially drilled receptacle for receiving a solid resilient plug 82. The plug is larger than the receptacle which captures the plug and a portion projects beyond the rod 80 to seat and seal in the drilled hole 83. Sealing is accomplished on closure into the hole 83.

The advantages and features of the disclosed apparatus were identified heretofore. Now that the structure has been described, its mode of operation to accomplish these advantages should be considered. Briefly, the normal position for the check valve element 30 is the closed position detailed in FIG. 2. The passage from the cavity 20 is filled, and the dead volume in this area is substantially nil, and there is no loss of volume on taking a sample. This results from the filling of the passage beginning at 27 and extending to the seal ring 32 by the conforming tip of the valve 30.

Assume that pipeline pressure fluctuates over wide limits. Even so, the fluctuations do not create a problem. Pipeline pressure is exposed to both ends of the valve 30 so that it is in a neutral state. It is not moved by pipeline pressure. It is not biased one direction or the other by pipeline pressure. As installed, it stays closed by the weight of gravity acting on the valve element and the small spring 58. Pressure balancing of the valve 30 by applying pressure to both ends eliminates pressure dependent fluctuations.

Several benefits flow from this. It is not necessary to install a different spring for each pipeline pressure. It is not necessary to incorporate an extremely large diaphragm to be able to overcome forces resulting from pipeline pressure increases. In fact, the pressure balance across the valve 30 enables the device to operate over a wide range of pressures, whether static or dynamic.

Back pressure variations do not impact operation of the valve 30. Assume that the back pressure (at the sample storage bottle) is either fixed or increases as sample accumulation occurs. In either case, back pressure, in the annulus 33, does not alter the operation of the valve 30. When closed, it is exposed to the back pressure absent facing shoulders and, therefore, no imbalancing forces are created. When the valve 30 is open, any back pressure which acts in the annular space 33 is overcome by the pressure of the fluid being pumped from the chamber 20. A number of scale factors have been noted in this disclosure, but they are related primarily to relative scale factors such as the relative cross-sectional area within the seal 32 contrasted with the seal 53. The device can be sized to relatively large sizes dependent on the pumping requirements. If desired, the sampling rate can be altered by modification of the number of strokes in a given interval to increase the sample removed.

The sample collection means (the resilient plug 18) can be a solid metal piston in a cylinder to pressurize the sample. In this event, the fluid sample is again forced into the check valve in the same fashion as described above.

While the foregoing is directed to the preferred embodiment, the scope is determined by the claims which follow.

I claim:

1. Sample collection apparatus comprising:
   (a) an elongate hollow body adapted to have one end extended into a container having a volume of fluid therein to be sampled, said body having a remote end extending away from the container;
   (b) sample gathering means at the one end of said body for insertion into the fluid to be sampled;
   (c) sample outlet passage means communicating from said sample gathering means and comprising an opening in a wall of said sample gathering means and extending to a sample outlet port for delivery of a sample;
   (d) valve means cooperative with said sample outlet passage means, said valve means extending into the opening of said wall for closing said sample outlet passage means;
   (e) wherein said valve means comprises a circular valve seat and circular resilient seal surface means conforming in size and shape to said seat to seat and seal thereagainst; and
   (f) wherein said resilient seal means is supported by a reciprocating rod, said rod extending along and within said sample outlet passage means and wherein said rod reciprocates said seal means to a closed position relative to said valve seat to reduce the dead volume thereof.

2. Sample collecting apparatus comprising:
   (a) an elongate hollow body adapted to have one end extended into a container having a volume of fluid therein to be sampled, said body having a second end remote from the container;
   (b) sample gathering means at the one end of said body for insertion into a fluid to be sampled;
   (c) sample outlet passage means communicating from said sample gathering means and extending therefrom through a hole in said body to gather sample;
   (d) check valve means including a valve seat at said hole and check valve element means cooperative with said seat to close said check valve means, said check valve means being located serially at said hole to prevent fluid flow along said sample outlet passage means;

(e) means for applying pressure from the container to first and second opposing faces of said check valve element means to create a balanced force acting thereacross, and wherein said check valve element means is exposed to a pressure differential force below a specified value; and (f) said check valve element means comprises an elongate rod having opposite ends, one end of said rod having an exposed shoulder adjacent to a first seal means, and the opposite end thereof comprising a second seal means defining a cross-sectional area wherein the area within said first and second seal means are equal; and (g) fluid flow means adapted to be extended from the container to a closed chamber surrounding said one end of said rod and exposing said rod to fluid from the container to create a balancing force acting thereacross.

3. The apparatus of claim 2 wherein:

said rod is grooved at said other end to support said second seal means;

said second seal means sealing at said valve seat;

and also including an elongate passage in said elongate hollow body to receive said elongate rod, said passage having a length sufficient to enable said rod to move longitudinally therein and further including means positioning said first and second seal means and said cooperative shoulder for sealing and sliding axial movement between open and closed positions for said check valve means.

4. The apparatus of claim 2 wherein said first and second opposing faces are equal in area.

5. The apparatus of claim 2 wherein said first and second opposing faces are equal in area and said first face is formed by an elongate rod extension on said check valve element means exposed to sample fluid pressure acting thereon; and wherein said second face is defined by an opposing area on said check valve element means and said opposing area is permanently exposed to fluid pressure from the container.

6. Sample collection apparatus comprising:

(a) an elongate hollow body adapted to have one end extended into a container having a volume of fluid therein to be sampled, said body having a remote end extending away from the container;

(b) sample gathering means at the one end of said body for insertion into the fluid to be sampled;

(c) sample outlet passage means communicating from said sample gathering means and comprising an opening in a wall of said sample gathering means and extending to a sample outlet port for delivery of a sample;

(d) valve means cooperative with said sample outlet passage means, said valve means extending into the opening of said wall for closing said sample outlet passage means;

(e) a valve seat adjacent to and surrounding an opening for admitting fluid to be sampled;

(f) an elongate, rod shaped valve element having a tapered tip wherein said tip is conformed to seat against said valve seat to reduce the dead volume thereof;

(g) a cooperative groove and seal means in said groove sealing against fluid flow through said valve seat; and (h) means for reciprocating said rod.

* * * * *